United States Patent
Fujimoto

(10) Patent No.: US 8,663,090 B2
(45) Date of Patent: Mar. 4, 2014

(54) ENDOSCOPE CLEANING SHEATH

(75) Inventor: Ryuhei Fujimoto, Kokubunji (JP)

(73) Assignee: Olympus Medical Systems Corp., Tokyo (JP)

( * ) Notice: Subject to any disclaimer, the term of this patent is extended or adjusted under 35 U.S.C. 154(b) by 395 days.

(21) Appl. No.: 12/939,526

(22) Filed: Nov. 4, 2010

(65) Prior Publication Data

US 2011/0230716 A1 Sep. 22, 2011

Related U.S. Application Data

(63) Continuation of application No. PCT/JP2010/059911, filed on Jun. 11, 2010.

(30) Foreign Application Priority Data

Jun. 22, 2009 (JP) ................................ 2009-147897

(51) Int. Cl.
 *A61B 1/00* (2006.01)
(52) U.S. Cl.
 USPC ............ 600/114; 600/141; 600/156; 600/157
(58) Field of Classification Search
 USPC ......... 600/121–125, 139–152, 155–159, 104, 600/106, 107, 114–116; 604/523–528
 See application file for complete search history.

(56) References Cited

U.S. PATENT DOCUMENTS 5,989,183 A 11/1999 Reisdorf et al.
2005/0085694 A1* 4/2005 Nakao ........................... 600/153

(Continued)

FOREIGN PATENT DOCUMENTS

JP 07-184836 7/1995
JP 07-194524 8/1995

(Continued)

OTHER PUBLICATIONS

Abstract of International Publication No. WO 2005/072402 A2, dated Aug. 11, 2005.

(Continued)

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

An endoscope cleaning sheath includes a flexible tube body that is mounted to an insertion portion having a bending portion included in an endoscope, and that has a plurality of through-holes parallel to a longitudinal axis; and a cylindrical distal end nozzle that is provided at a distal end portion of the flexible tube body and that sprays at least one of a gas and a liquid at least at an observation window provided at a distal end portion of the insertion portion of the endoscope. The through-holes are a hole for an endoscope insertion portion through which the insertion portion of the endoscope is inserted, and at least a first fluid conduit that supplies gas and a second fluid conduit that supplies liquid. The first fluid conduit and the second fluid conduit are provided at positions in a direction that is different from a bending direction of the bending portion of the insertion portion that is inserted and disposed in the hole for an endoscope insertion portion. The flexible tube body includes a sheath bending portion that covers a circumference of the bending portion of the insertion portion that is inserted and disposed in the hole for an endoscope insertion portion. The sheath bending portion includes at least one concave portion or hole that decreases a bending resistance of the sheath bending portion to a resistance that is less than a bending resistance of the flexible tube body.

1 Claim, 11 Drawing Sheets

(56) References Cited

U.S. PATENT DOCUMENTS

| | | | |
|---|---|---|---|
| 2007/0225559 A1* | 9/2007 | Clerc et al. | 600/117 |
| 2008/0188715 A1 | 8/2008 | Fujimoto | |
| 2009/0143647 A1* | 6/2009 | Banju | 600/149 |

FOREIGN PATENT DOCUMENTS

| | | |
|---|---|---|
| JP | 8-501720 | 2/1996 |
| JP | 08-140922 | 6/1996 |
| JP | 10-225435 | 8/1998 |
| JP | 11-104066 | 4/1999 |
| JP | 2002-065592 | 3/2002 |
| JP | 2007-522837 | 8/2007 |
| JP | 2008-093173 | 4/2008 |
| JP | 2008-132282 | 6/2008 |
| WO | WO 95/02988 | 2/1995 |

OTHER PUBLICATIONS

International Search Report dated Sep. 14, 2010.
US 5,772,579, 6/1998, Reisdorf et al. (withdrawn).

* cited by examiner

ENDOSCOPE CLEANING SHEATH

CROSS REFERENCE TO RELATED APPLICATION

This application is a continuation application of PCT/JP2010/059911 filed on Jun. 11, 2010 and claims benefit of Japanese Application No. 2009-147897 filed in Japan on Jun. 22, 2009, the entire contents of which are incorporated herein by this reference.

BACKGROUND OF THE INVENTION

1. Field of the Invention

The present invention relates to an endoscope cleaning sheath that sprays a mixed fluid in an atomized state at an observation window or the like of an endoscope to remove adherents that adhere to the observation window or the like.

2. Description of the Related Art

When in-vivo mucus, blood, fat, dirt or the like adhere to an observation window or illuminating window or the like of an endoscope during endoscopic observation, favorable observation is hindered.

Japanese Patent Application Laid-Open Publication No. 2008-132282, for example, discloses a sheath for cleaning an endoscope to solve the problems caused by such adherence. This sheath for cleaning an endoscope includes a wiper unit that removes adherents on an observation window or adherents on an illuminating window. The length of a blade included in the wiper unit is sufficient for removing adherents and prevents the hindrance of endoscopic observation when conducting observation or treatment. The sheath for cleaning an endoscope includes a sheath insertion portion and a sheath body portion. An insertion portion of a rigid endoscope is inserted into the sheath insertion portion. The sheath body portion is fixed to an operation portion of the rigid endoscope. According to the sheath for cleaning an endoscope, adhered dirt can be removed by manually operating the blade of the wiper unit.

It is conventionally known that superior cleaning performance can be obtained by spraying a mixed fluid in an atomized state from an ejection nozzle towards an outer surface of an observation window in comparison to a case of spraying only water at the outer surface of the observation window. A sheath for cleaning an endoscope disclosed in Japanese Patent Application Laid-Open Publication No. 2008-093173 quickly removes adherents that are adhered to an observation window or the like of an endoscope by spraying a mixed fluid formed by mixing water and air in an atomized state at the observation window or the like. The sheath for cleaning an endoscope mainly includes, in order from the distal end side thereof, a distal-end structure section and a tube body. A hole through which the insertion portion of the endoscope is inserted and a plurality of fluid conduits that serve as conduits for water or air are provided in the tube body.

When the endoscope is an endoscope with a bending mechanism that includes a bending portion in the insertion portion, the sheath body portion or tube body included in the sheath for cleaning an endoscope is constituted by a flexible multi-lumen tube. It is thereby possible for the bending portion to bend in a state in which the sheath for cleaning an endoscope is mounted to the endoscope.

SUMMARY OF THE INVENTION

An endoscope cleaning sheath of the present invention includes a flexible tube body that is mounted to an insertion portion having a bending portion included in an endoscope and that has a plurality of through-holes that are parallel to a longitudinal axis, and a cylindrical distal-end structure section that is provided at a distal end portion of the flexible tube body and that sprays at least one of a gas and a liquid at least at an observation window provided at a distal end portion of the insertion portion of the endoscope, wherein: the through-holes are a hole for an endoscope insertion portion through which the insertion portion of the endoscope is inserted, and at least a first fluid conduit that supplies the gas and a second fluid conduit that supplies the liquid; the first fluid conduit and the second fluid conduit are provided at positions in a direction that is different from a bending direction of the bending portion of the insertion portion that is inserted and disposed in the hole for an endoscope insertion portion; and the flexible tube body includes a sheath bending portion that covers a circumference of the bending portion of the insertion portion that is inserted and disposed in the hole for an endoscope insertion portion, and the sheath bending portion includes at least one concave portion or hole that decreases a bending resistance of the sheath bending portion to a resistance that is less than a bending resistance of the flexible tube body.

BRIEF DESCRIPTION OF THE DRAWINGS

FIG. 1 is a view that illustrates an endoscope apparatus that includes a rigid endoscope with a bending function and a cleaning sheath;

FIG. 2 is a front view of a state in which an insertion portion of the endoscope is inserted through a hole for an endoscope insertion portion of the cleaning sheath;

FIG. 3 is a cross-sectional view along a line III-III in FIG. 1 that illustrates a configuration of a multi-lumen tube included in the cleaning sheath;

FIG. 4 is a view showing a state in which the insertion portion of the endoscope is mounted in a hole for an endoscope insertion portion of the endoscope cleaning sheath;

FIG. 5 is a cross-sectional view along a line V-V in FIG. 1 that illustrates a sheath bending portion that has a concave portion in an upper outer circumferential face between conduits of the multi-lumen tube;

FIG. 13 is a view that illustrates a cleaning sheath that has a sheath bending portion of a different configuration;

FIG. 14 is a cross-sectional view along a line XIV-XIV in FIG. 13; and

FIG. 16 is a perspective view that illustrates a sheath bending portion in which a plurality of communicating holes are arranged;

FIG. 17 is a view of an insertion portion mounting section as viewed from an upper direction; and FIG. 18 is a cross-sectional view along a line XVIII-XVIII in FIG. 17.

FIG. 19 is a perspective view that illustrates a sheath bending portion in which a plurality of communicating holes are arranged that have different length dimensions in the longitudinal direction;

FIG. 20 is a cross-sectional view along a line XX-XX in FIG. 19; and

FIG. 21 is a view that illustrates the relation between the curvature of the bending portion and a plurality or kinds of communicating holes that are provided in the sheath bending portion.

DETAILED DESCRIPTION OF THE PREFERRED EMBODIMENT(S)

Embodiments of the present invention are described hereunder with reference to the drawings.

A first embodiment of the present invention will be described referring to FIG. 1 to FIG. 5.

Figure 1:
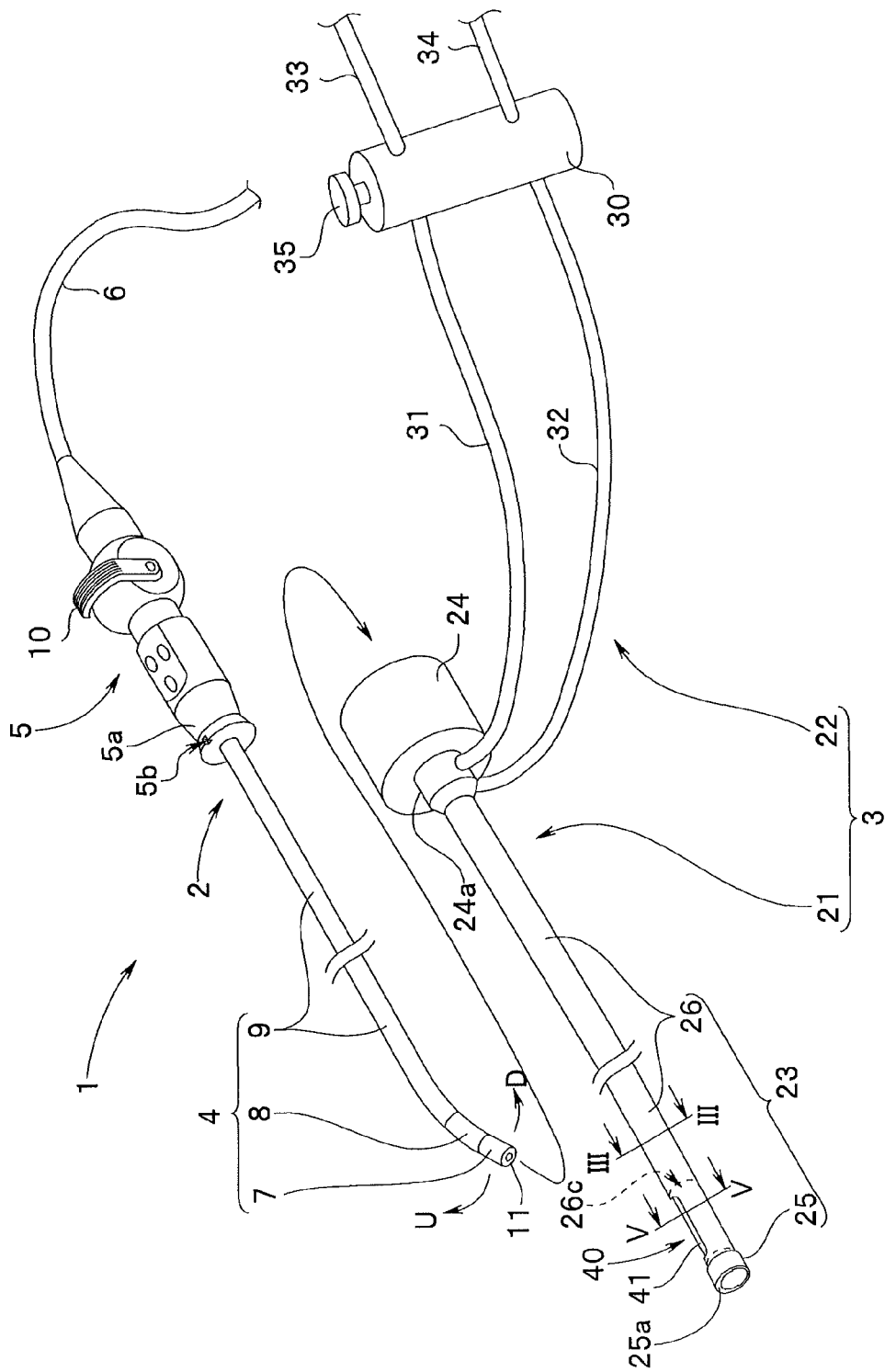
FIG. 1 to FIG. 5 relate to a first embodiment of the present invention.

As shown in FIG. 1, an endoscope apparatus 1 of the present embodiment mainly includes a rigid endoscope with a bending function (hereunder, abbreviated to "endoscope") 2 and an endoscope cleaning sheath (hereunder, abbreviated to "cleaning sheath") 3.

The endoscope 2 includes an insertion portion 4, an operation portion 5, and a universal cord 6. The universal cord 6 extends from the operation portion 5 and is connected to a video processor that is an external apparatus. The video processor performs signal processing of video signals that are picked up with an image pickup device denoted by reference numeral 14 in FIG. 2, control for adjusting the gain of the image pickup device 14 and the like, and output of a driving signal for driving. The operation portion 5 is provided at the rear end of the insertion portion 4. A bending knob 10 and various switches are provided in the operation portion 5. The various switches include switches that control the image pickup device and, for example, instruct the image pickup device to perform image pickup operations such as a freeze operation and a release operation.

The insertion portion 4 includes, in order from the distal end side, a rigid distal end portion 7, a bendable bending portion 8, and a rigid and elongated rigid portion 9. In the present embodiment, the bending portion 8, for example, bends in the upward and downward directions as indicted by an arrow U and an arrow D in the figures. More specifically, the bending portion 8 is configured so that, when the surgeon appropriately operates the bending knob 10, the bending portion 8 bends in the upward direction or the downward direction in accordance with the relevant operation.

The bending directions of the bending portion 8 are not limited to the upward and downward directions, and the bending portion 8 may be configured to bend in the upward and downward directions as well as the left and right directions and the like.

Figure 2:
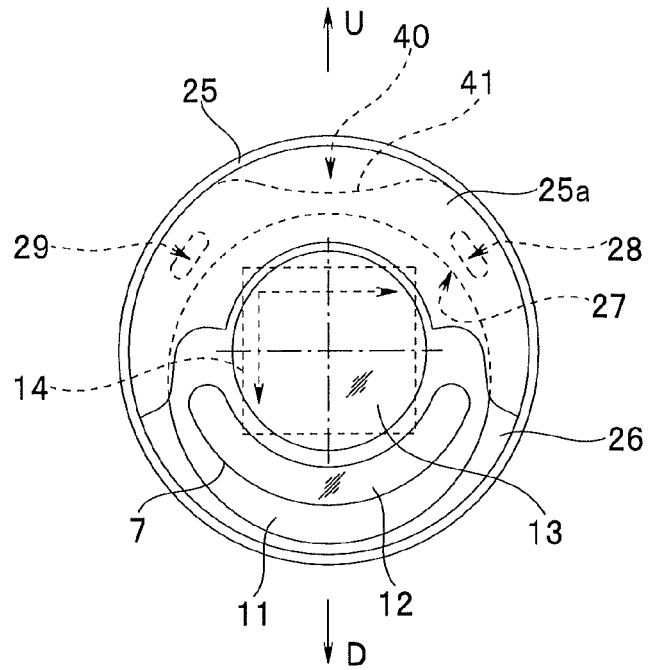

As shown in FIG. 2, an illuminating window 12 for emitting illuminating light and an observation window 13 for performing observation are provided in a distal end face 11 of the distal end portion 7 of the endoscope 2. An optical image incident on the observation window 13 forms an image on a light-receiving face of the image pickup device 14 provided inside the distal end portion 7. A video signal picked up by the image pickup device 14 is subjected to signal processing by the video processor and is thereafter displayed on a screen of an unshown display apparatus.

The light-receiving face of the image pickup device 14 is orthogonally arranged with respect to the longitudinal axis of the insertion portion 4. A vertical transfer direction V of the image pickup device 14 matches the vertical direction of the screen, and a lateral direction matches a horizontal transfer direction H. Specifically, the vertical directions of an endoscope image picked up by the image pickup device 14 match the vertical and lateral directions of the screen.

The vertical directions of the bending portion 8 included in the insertion portion 4 are set so as to correspond to the vertical and lateral directions of an endoscope image displayed on the screen. More specifically, the vertical directions of the bending portion 8 correspond to the vertical directions of an endoscope image displayed on the screen. Accordingly, when the surgeon operates the bending knob 10 to bend the bending portion 8 in the downward direction, the bending portion 8 bends in the downward direction accompanying that operation. At such time, the endoscope image that is being displayed on the screen changes accompanying the bending of the bending portion 8 so as to allow observation in the downward direction.

As shown in FIG. 1, the cleaning sheath 3 mainly includes a mounting section 21 and a fluid supply portion 22.

The mounting section 21 includes an insertion portion mounting section 23 and an operation portion attaching section 24. The insertion portion mounting section 23 includes a distal end nozzle 25 as a distal-end structure section and a multi-lumen tube 26. The multi-lumen tube 26 includes a plurality of through-holes that are elongated parallel to the longitudinal axis. The multi-lumen tube 26 is a flexible tube body that has a cross section as shown in FIG. 3.

The multi-lumen tube 26 includes a sheath bending portion 40 on the distal end nozzle 25 side that is one end portion. The through-holes of the multi-lumen tube 26 are a large-diameter hole for an endoscope insertion portion 27 and a pair of small-diameter fluid conduits 28 and 29. The hole for an endoscope insertion portion 27 is an insertion passage through which the insertion portion 4 of the endoscope 2 is inserted. The first fluid conduit 28 is a gas delivery conduit for supplying a gas, and the second fluid conduit 29 is a liquid delivery conduit for supplying a liquid.

Figure 3:
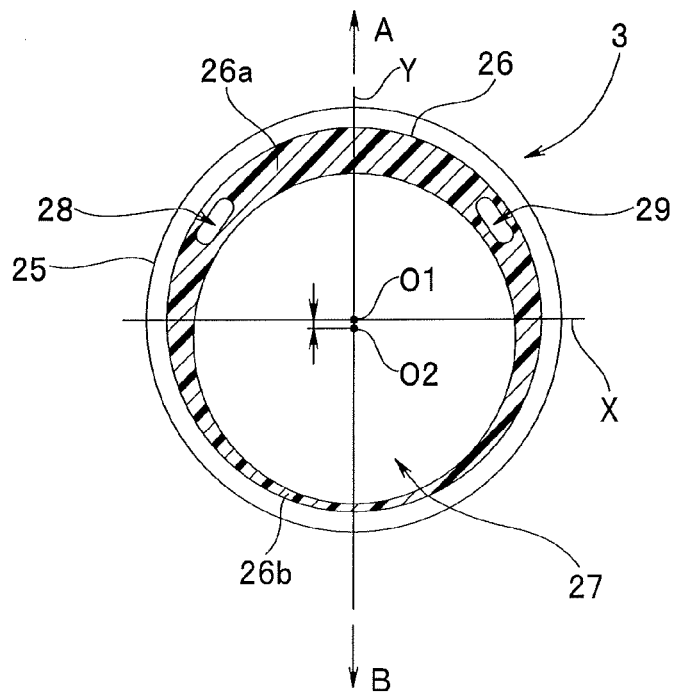

A central axis O2 of the hole for an endoscope insertion portion 27 is eccentric with respect to a central axis O1 of the multi-lumen tube 26 as indicated by arrows in the Y-axis direction in FIG. 3. Accordingly, in the multi-lumen tube 26, the wall thickness at the circumference of the hole for an endoscope insertion portion 27 differs between the upper side and lower side in the FIG. 3 in a manner that sandwiches the X axis in FIG. 3. The multi-lumen tube 26 has fluid conduits 28 and 29 in a thick-walled region 26a that has a thick wall thickness. The fluid conduits 28 and 29 are provided in a symmetrical positional relationship with a predetermined distance therebetween in a manner that sandwiches the Y axis. In the cleaning sheath 3, the direction of an arrow A is set as the upward direction and the direction of an arrow B is set as the downward direction in a manner that sandwiches the Y axis.

In this connection, reference numeral 26b denotes a thin-walled region. The thin-walled region 26b is a section at which the wall thickness of the multi-lumen tube 26 is thin. The thin-walled region 26b has a configuration in which the cross-sectional area is reduced to facilitate expansion of the multi-lumen tube 26 and decrease a reactive force of the tube itself to lessen the load at the time of bending.

Figure 4:
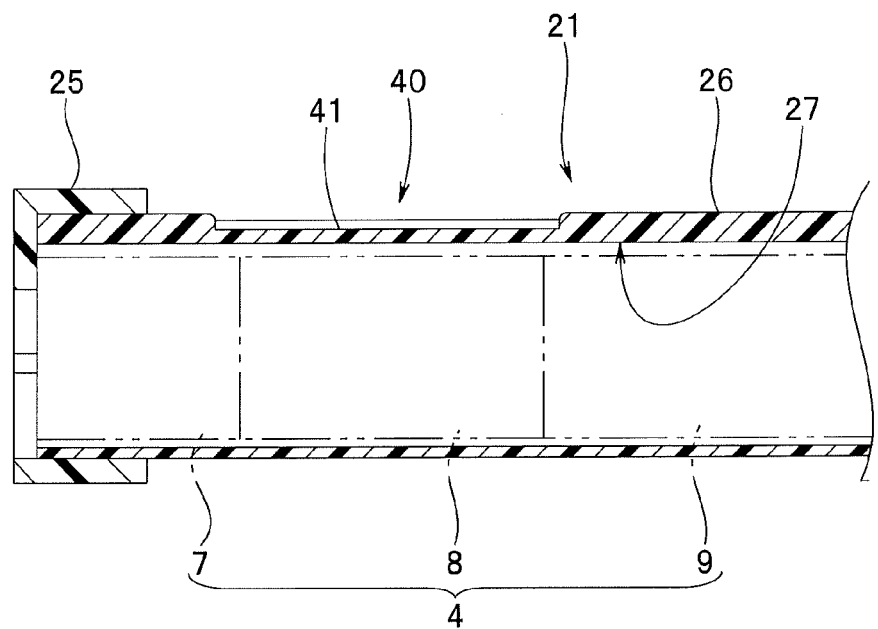

As shown in FIG. 1, the sheath bending portion 40 is provided in a bending portion disposition area 26c on a distal end side of the multi-lumen tube 26. Therefore, when the insertion portion 4 of the endoscope 2 is inserted into and disposed inside the hole for an endoscope insertion portion 27 as shown in FIG. 4, the circumference of the bending portion 8 is covered by the sheath bending portion 40. At this time, the vertical direction of the bending portion 8 matches the vertical direction of the multi-lumen tube 26.

Figure 5:
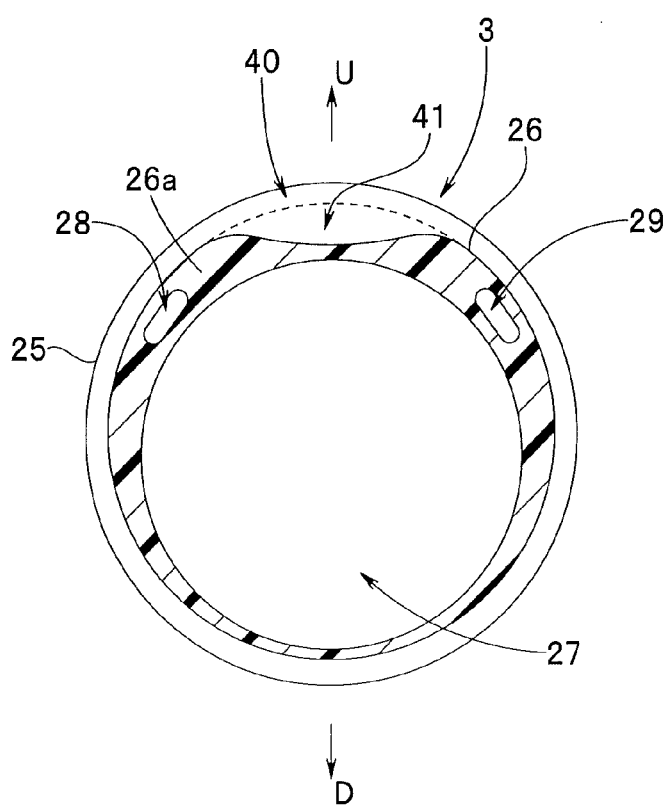

As shown in FIG. 1 and FIG. 5, the sheath bending portion 40 is provided with a concave portion 41 that is elongated parallel to the longitudinal axis of the multi-lumen tube 26. The concave portion 41 is provided in an upper outer circumferential face between the first fluid conduit 28 and the second fluid conduit 29 of the multi-lumen tube 26.

The concave portion 41 is a recessed part that reduces the thickness of the thick-walled region 26a in the upper direction of the multi-lumen tube 26. The concave portion 41 serves to reduce a resistance such as a load applied to a bending operation when the bending portion 8 is bent. The concave portion 41 is set so as to secure a wall thickness of a predetermined amount at the circumference of the fluid conduits 28 and 29. Thus, when the bending portion 8 is bent in the upward direction, although a force in a direction that compresses the tube is applied to the tube, the concave portion 41 changes shape and absorbs a force that attempts to push and contract the tube. As a result, a meandering portion is formed in the surface of the multi-lumen tube 26 that is disposed on the inner circumferential side of the bending portion, and crushing of the fluid conduits 28 and 29 is prevented.

The length dimensions in the longitudinal direction of the concave portion 41 are approximately the same as those in the longitudinal direction of the bending portion disposition area 26c. The width dimensions of the concave portion 41 are appropriately set in consideration of the wall thickness around the fluid conduits 28 and 29, and the depth dimensions are appropriately set in consideration of the bending resistance.

The distal end nozzle 25 is cylindrical, and is fixedly provided at the distal end portion of the multi-lumen tube 26. The distal end nozzle 25 has a distal end face portion 25a that is formed by notching in a predetermined shape as shown in FIG. 2. The inner face of the distal end face portion 25a is configured so as to contact with the distal end face 11 of the distal end portion 7. A T-shaped groove (not shown) that constitutes a flow channel is formed in the inner face of the distal end face portion 25a. For example, at least one of water and air is supplied via the fluid conduits 28 and 29 to the T-shaped groove. In this connection, the T-shaped groove is as described in detail in Japanese Patent Application Laid-Open Publication No. 2008-93173.

The operation portion attaching section 24 is cylindrical as shown in FIG. 1. The operation portion attaching section 24 has an unshown concave portion with which a distal end portion 5a of the operation portion 5 engages. For example, a convex portion that serves as a positioning portion is provided at a predetermined position in the concave portion. The convex portion is, for example, formed at a position that corresponds to the upward direction of the multi-lumen tube 26. The convex portion is engagingly inserted into a concave portion 5b formed in the distal end portion 5a of the operation portion 5. The concave portion 5b is formed at a position that corresponds to the upward direction of the bending portion 8.

The fluid supply portion 22 includes a spray switch 30, and a first gas delivery tube 31, a first liquid feed tube 32, a second gas delivery tube 33, and a second liquid feed tube 34 that are fluid tubes that have one end and another end.

One end portion of the first gas delivery tube 31 is connected to a predetermined position of, for example, a distal end side convex portion 24a of the operation portion attaching section 24. One end portion of the first liquid feed tube 32 is connected to a predetermined position of, for example, the distal end side convex portion 24a of the operation portion attaching section 24. The gas delivery tube 31 communicates with the first fluid conduit 28, and the liquid feed tube 32 communicates with the second fluid conduit 29.

Another end portion of the first gas delivery tube 31 is connected to a gas outlet of the spray switch 30, and another end portion of the first liquid feed tube 32 is connected to a liquid outlet of the spray switch 30.

Further, one end portion of the second gas delivery tube 33 is connected to a gas inlet of the spray switch 30, and one end portion of the second liquid feed tube 34 is connected to a liquid inlet of the spray switch 30. Another end portion of the second gas delivery tube 33 is connected to an unshown gas feed pump, and another end portion of the second liquid feed tube 34 is connected to an unshown liquid feed tank.

The spray switch 30 has a switching button 35 that can perform a switching operation in two stages. According to the present embodiment, when the surgeon performs an operation to push in the switching button 35 as far as a first stage, a gas is ejected from the distal end nozzle 25 towards the observation window 13 or the like. Further, when the surgeon performs an operation to push in the switching button 35 as far as a second stage, a mixed fluid formed by mixing air and water is sprayed from the distal end nozzle 25 towards the observation window 13 or the like.

Next, mounting of the cleaning sheath 3 to the insertion portion 4 is described.

The user mounts the cleaning sheath 3 to the insertion portion 4 of the endoscope 2. At that time, the user inserts the distal end of the insertion portion 4 into the hole for an endoscope insertion portion 27 of the multi-lumen tube 26 included in the cleaning sheath 3 from the operation portion attaching section 24 side. At such time, the user matches the vertical direction of the cleaning sheath 3 with the vertical direction of the bending portion 8.

The user integrally attaches the operation portion attaching section 24 of the cleaning sheath 3 to the operation portion 5 of the endoscope 2. Finally, the user engages the convex portion of the operation portion attaching section 24 with the concave portion 5b formed in the distal end portion 5a. As a result, the inner face of the distal end face portion 25a of the distal end nozzle 25 contacts the distal end face 11 of the distal end portion 7, to thereby complete mounting of the cleaning sheath 3 to the insertion portion 4.

In this mounted state, the sheath bending portion 40 covers the circumference of the bending portion 8. Further, as shown in FIG. 2, because the vertical direction of the bending portion 8 and the vertical direction of the cleaning sheath 3 match, the concave portion 41 of the sheath bending portion 40 is disposed in the upper direction of the bending portion 8 and the fluid conduits 28 and 29 provided in the cleaning sheath 3 are arranged at positions that are in a different direction from the bending direction of the bending portion 8 of the endoscope 2.

When the surgeon appropriately operates the bending knob 10 in this mounted state, the bending portion 8 that is covered by the multi-lumen tube 26 of the cleaning sheath 3 bends in the upward direction or downward direction in accordance with the operation of the bending knob 10. At this time, since the fluid conduits 28 and 29 are arranged at positions that are in a different direction from the bending direction of the bending portion 8 of the endoscope 2 as described above, crushing of the fluid conduits 28 and 29 by the bending of the bending portion 8 can be prevented. Thus, a problem whereby the fluid conduits 28 and 29 provided in the cleaning sheath 3 are flattened accompanying the bending of the bending portion 8 and it is difficult to secure a flow quantity is prevented.

Further, as described above, the concave portion 41 of the sheath bending portion 40 that covers the circumference of the bending portion 8 is positioned in the upper direction of the bending portion 8, and the thin-walled region 26b is positioned in the lower direction of the bending portion 8. Accordingly, a bending operation of the bending portion 8 can be smoothly performed by operating the bending knob 10. In addition, when the bending portion 8 has been bent, it is possible to prevent the occurrence of a meandering portion at the inner circumferential side thereof.

By means of the concave portion 41, the resistance of the thick-walled region 26a of the multi-lumen tube 26 is reduced and the wall thickness of the fluid conduits 28 and 29 that are arranged at positions that are different from the bending direction of the bending portion 8 is secured. Accordingly, when the bending portion 8 has been bent in the upward direction, even if slackness or creasing occurs in the multi-lumen tube 26 that is disposed on the inner circumferential side of the bending portion 8, a compressive force applied to the thick-walled region 26a decreases. Hence, it is possible to prevent creasing generated in the multi-lumen tube 26 from changing shape into a meandering portion that crushes the fluid conduits 28 and 29, and thus crushing of the fluid conduits 28 and 29 can be prevented.

Figure 6:
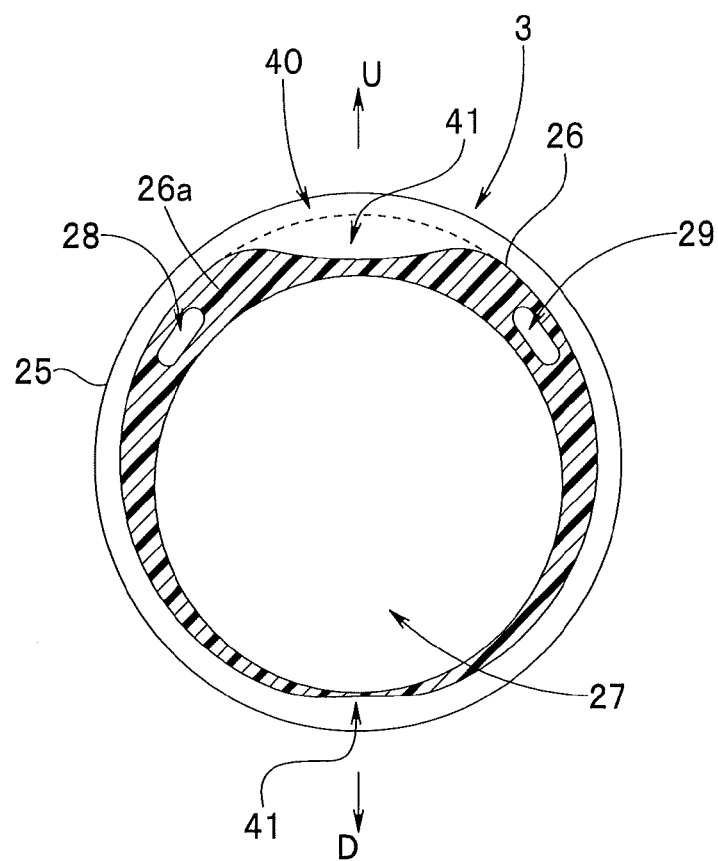
FIG. 6 is a cross-sectional view that illustrates a sheath bending portion in which a concave portion that faces a concave portion provided in the upper outer circumferential face between conduits of the multi-lumen tube is provided in a lower outer circumferential face.

A configuration may also be adopted in which a concave portion 41 is provided that reduces the amount of force applied to the thick-walled region 26a and in which, as shown in FIG. 6, on the thin-walled region 26b side, a concave portion 41 is provided at a lower part of the bending portion 8 facing the concave portion 41 to thereby decrease the cross-sectional area of the tube itself.

Thus, when the bending portion 8 is bent, a force that attempts to push and contract the multi-lumen tube 26 that arises on the inner circumferential side of the bend and a force that attempts to expand the multi-lumen tube 26 that arises on the outer circumferential side of the bend can be simultaneously reduced, so that an effect can be exerted that reduces a load applied to the bending portion 8 to the maximum degree.

Note that the configuration of the sheath bending portion 40 provided in the multi-lumen tube 26 is not limited to the above described configuration in which a concave portion that is parallel to the longitudinal axis is provided at an upper outer circumferential face between the first fluid conduit 28 and the second fluid conduit 29 of the multi-lumen tube 26 or at outer circumferential faces in the upper and lower directions, and the sheath bending portion may have the same configuration as a sheath bending portion illustrated in FIG. 7 to FIG. 12 that are described hereunder.

Hereunder, another configuration example of the sheath bending portion is described with reference to the drawings.

Figure 7:
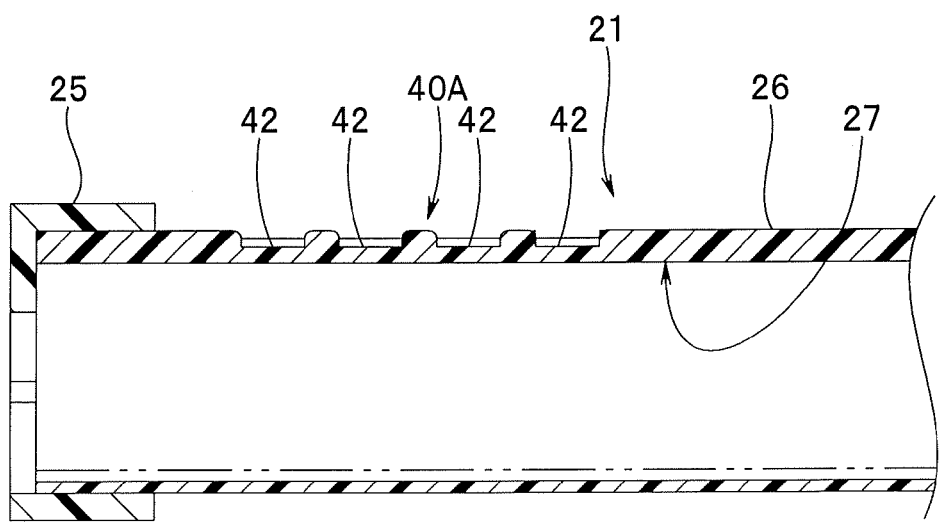
FIG. 7 is a cross-sectional view relating to a modification example of the sheath bending portion, that illustrates a sheath bending portion in which a plurality of concave portions are arranged.

FIG. 7 relates to a modification example of the sheath bending portion, and is a cross-sectional view that illustrates a sheath bending portion in which a plurality of concave portions are arranged.

In a sheath bending portion 40A of the present modification example, instead of a concave portion 41 provided parallel to the longitudinal axis, a plurality of concave portions 42 that are elongated in a circumferential direction are, for example, arranged at regular intervals parallel to the longitudinal axis.

By providing a plurality of concave portions 42 on the upper outer circumferential face of the multi-lumen tube 26 in this manner, actions and effects that are similar to those of the above described first embodiment can be obtained.

Figure 8:
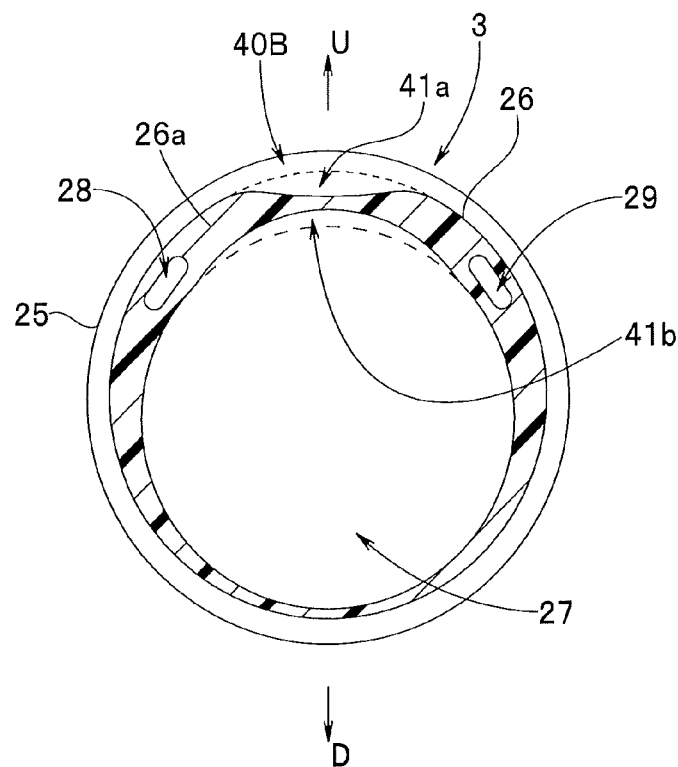
FIG. 8 is a cross-sectional view relating to another modification example of the sheath bending portion, that illustrates a sheath bending portion that has a concave portion in an outer circumferential face between upper conduits of a multi-lumen tube and in an inner circumferential face of a hole for an endoscope insertion portion.

FIG. 8 relates to another modification example of the sheath bending portion, and is a cross-sectional view that illustrates a sheath bending portion that has a concave portion in an outer circumferential face between conduits provided in the upper direction of the multi-lumen tube and in an inner circumferential face of a hole for an endoscope insertion portion.

A sheath bending portion 40B of the present modification example includes concave portions 41a and 41b that are parallel to the longitudinal axis in the upper outer circumferential face between the first fluid conduit 28 and the second fluid conduit 29 and in an inner circumferential face in the upper direction of the multi-lumen tube 26.

By providing the concave portion 41a in the upper outer circumferential face and providing the concave portion 41b in an inner circumferential face in the upper direction of the multi-lumen tube 26 in this manner, actions and effects that are similar to those of the above described embodiments can be obtained.

Figure 9:
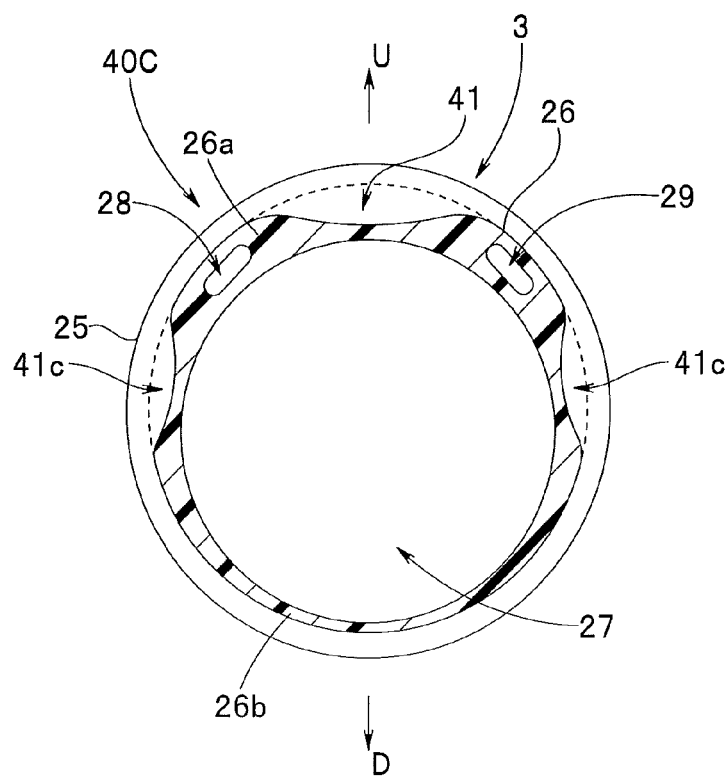
FIG. 9 is a cross-sectional view relating to another modification example of the sheath bending portion, that illustrates a sheath bending portion that has a plurality of concave portions in an outer circumferential face of a multi-lumen tube.

FIG. 9 relates to a further modification example of the sheath bending portion, and is a cross-sectional view that illustrates a sheath bending portion that has a plurality of concave portions in the outer circumferential face of the multi-lumen tube.

In addition to the concave portion 41 parallel to the longitudinal axis that is provided between the first fluid conduit 28 and the second fluid conduit 29 of the multi-lumen tube 26, a sheath bending portion 40C of the present modification example includes, for example, a pair of concave portions 41c that are parallel to the longitudinal axis in the thick-walled region 26a of the outer circumferential face between conduits in the downward direction from the fluid conduits 28 and 29.

By providing the concave portion 41 and concave portions 41c in the outer circumferential face of the multi-lumen tube 26 in this manner, actions and effects that are similar to those of the above described embodiments can be obtained.

Figure 10:
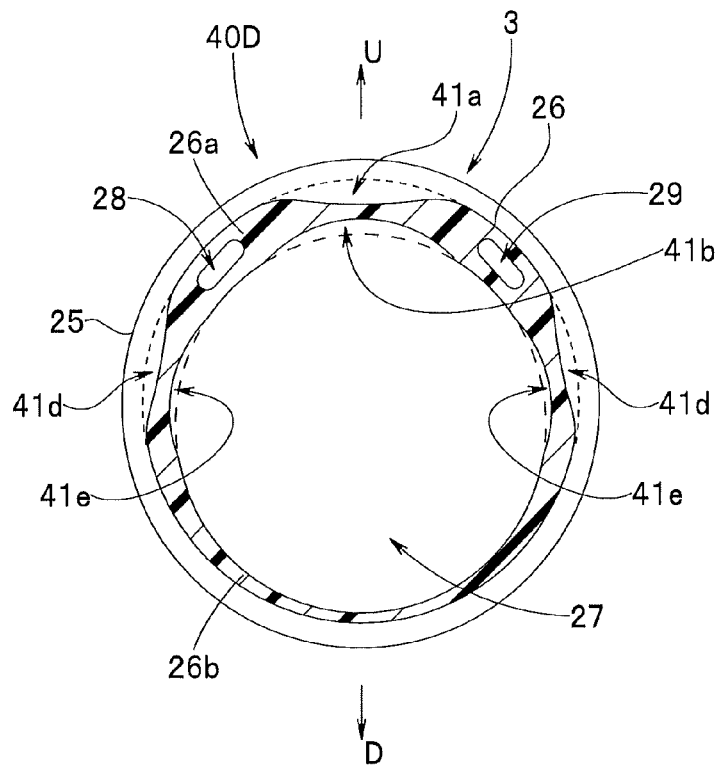
FIG. 10 is a cross-sectional view relating to a further modification example of the sheath bending portion, that illustrates a sheath bending portion that has a plurality of concave portions in the outer circumferential face of a multi-lumen tube and in the inner circumferential face of a hole for an endoscope insertion portion, respectively.

FIG. 10 relates to a further modification example of the sheath bending portion, and is a cross-sectional view that illustrates a sheath bending portion that has a plurality of concave portions in the outer circumferential face of a multi-lumen tube and in an inner circumferential face of a hole for an endoscope insertion portion, respectively.

In addition to the concave portion 41a parallel to the longitudinal axis that is provided in the upper outer circumferential face and the concave portion 41b parallel to the longitudinal axis that is provided in the inner circumferential face in the upward direction, a sheath bending portion 40D of the present modification example also includes a pair of concave portions 41d that are parallel to the longitudinal axis in the outer circumferential face of the thick-walled region 26a between the conduits in the downward direction from the fluid conduits 28 and 29 as well as a pair of concave portions 41e that are parallel to the longitudinal axis in the inner circumferential face of the multi-lumen tube 26.

By providing the concave portion 41a and concave portions 41d in the outer circumferential face and providing the concave portion 41b and the concave portions 41e in the inner circumferential face of the multi-lumen tube 26 in this manner, actions and effects that are similar to those of the above described embodiments can be obtained.

Figure 11:
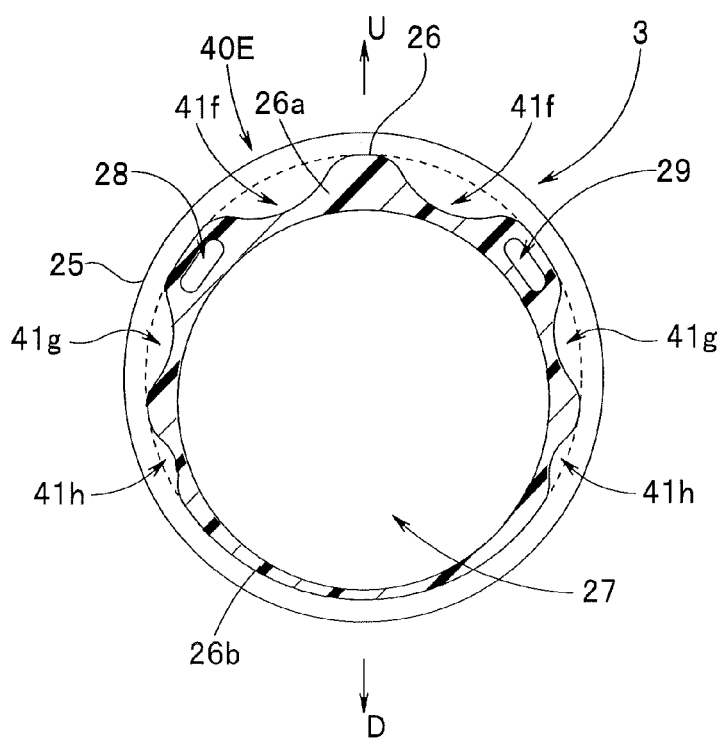
FIG. 11 is a cross-sectional view relating to a further modification example of the example shown in FIG. 9, that illustrates a sheath bending portion that has a plurality of concave portions in an outer circumferential face between respective conduits of a multi-lumen tube.

A configuration may also be adopted as shown in FIG. 11 in which a sheath bending portion 40E includes concave portions 41f, 41g, and 41h that are arranged in the outer circumferential face of the multi-lumen tube 26 at positions that are in a different direction from the bending direction of the bending portion 8. The sheath bending portion 40E includes the concave portions 41f, 41g, and 41h that are parallel to the longitudinal axis that serve to thin the thick-walled region 26a between upper conduits and between lower conduits composed between the first fluid conduit 28 and the second fluid conduit 29.

Figure 12:
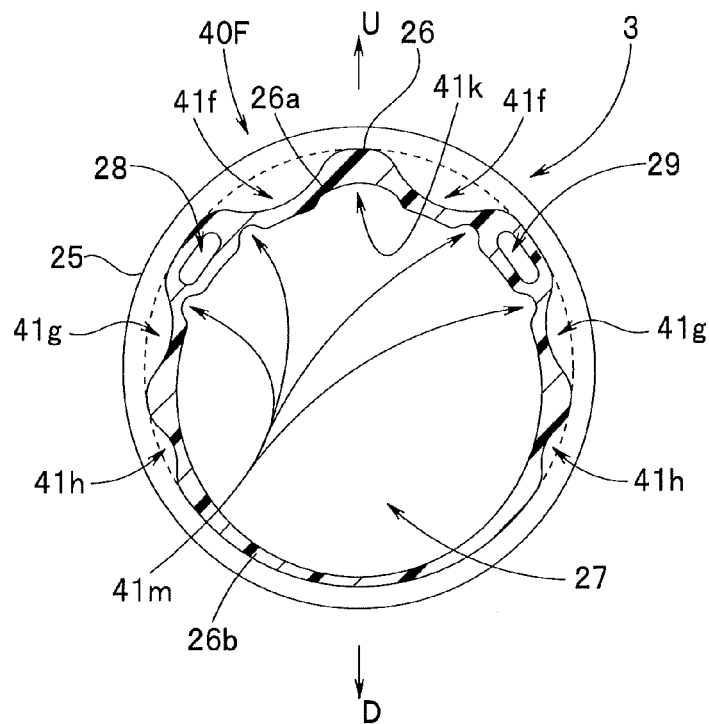
FIG. 12 is a cross-sectional view relating to a further modification example of the example shown in FIG. 11, that illustrates a sheath bending portion that has a plurality of concave portions in an outer circumferential face between respective conduits of a multi-lumen tube and in an inner circumferential face of a hole for an endoscope insertion portion.

Further, a sheath bending portion 40F shown in FIG. 12 includes, in addition to the concave portions 41f, 41g, and 41h, a concave portion 41k and a plurality of concave portions 41m that are parallel to the longitudinal axis and that are provided in the inner circumferential face of the hole for an endoscope insertion portion 27 to uniformize the wall thickness at the circumference of the hole for an endoscope insertion portion 27.

By providing the concave portions 41f, 41g, 41h, 41k, and 41m in the outer circumferential face and inner circumferential face of the multi-lumen tube 26 in this manner, actions and effects that are similar to those of the above described embodiments can be obtained.

Note that, in the embodiments illustrated in FIG. 7 to FIG. 12, a configuration may be adopted that reduces the cross-sectional area of the tube itself by providing a concave portion 41 at a lower part of the bending portion 8 opposite to the concave portion 41, as shown in FIG. 6, on the thin-walled region 26b side.

In this connection, the above described FIG. 11 relates to an additional modification example of the above described FIG. 9, and is a cross-sectional view that illustrates a sheath bending portion having a plurality of concave portions in the outer circumferential face between the conduits of the multi-lumen tube. Furthermore, the above described FIG. 12 relates to an additional modification example of the above described FIG. 11, and is a cross-sectional view that illustrates a sheath bending portion having a plurality of concave portions in the outer circumferential face between the conduits of the multi-lumen tube and in the inner circumferential face of the hole for an endoscope insertion portion.

Figure 13:
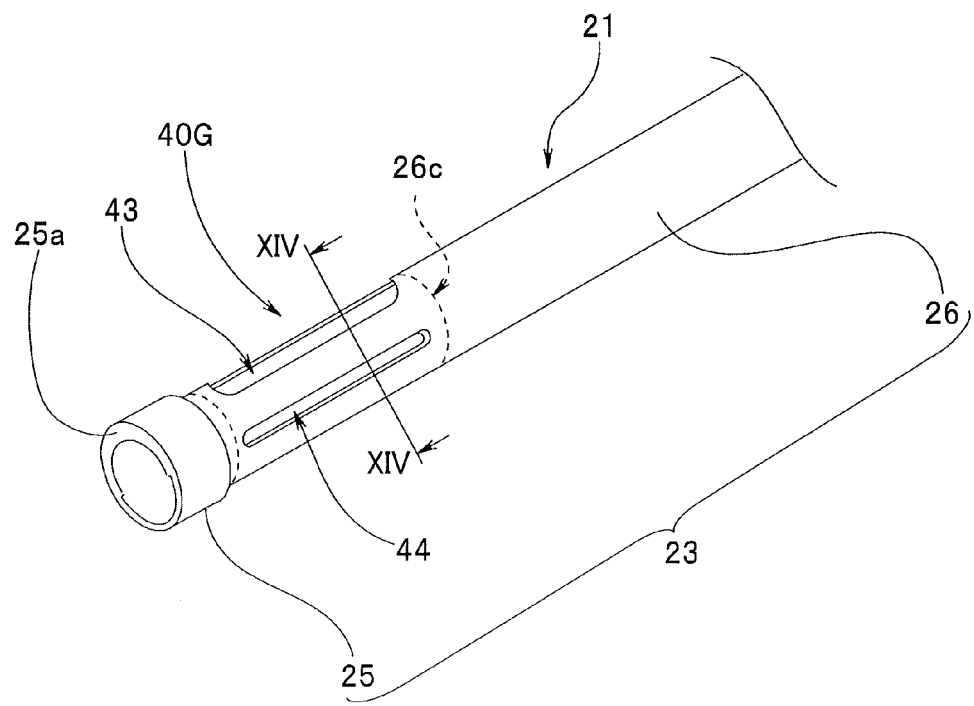
FIG. 13 and FIG. 14 relate to a second embodiment of the present invention.
Figure 14:
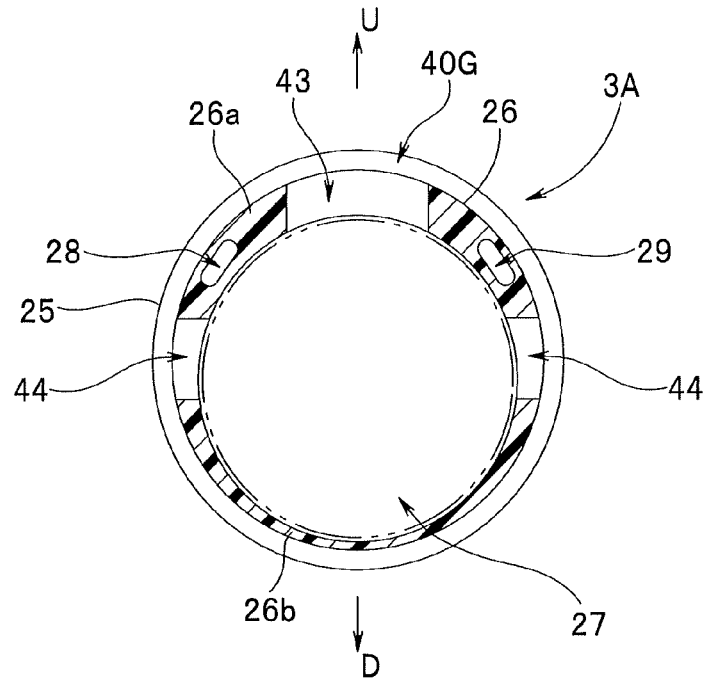

FIG. 13 and FIG. 14 relate to a second embodiment of the present invention. FIG. 13 is a view that illustrates a cleaning sheath that has a sheath bending portion of a different configuration. FIG. 14 is a cross-sectional view along a line XIV-XIV in FIG. 13.

In a cleaning sheath 3A of the present embodiment, a sheath bending portion 40G provided in the multi-lumen tube 26 includes holes 43 and 44.

More specifically, as shown in FIG. 13 and FIG. 14, the sheath bending portion 40G of the present embodiment includes communicating holes 43 and 44 formed in a long hole shape that are elongated parallel to the longitudinal axis of the multi-lumen tube 26. The communicating hole 43 is a single hole that allows the outside of the multi-lumen tube 26 to communicate with the inside of the hole for an endoscope insertion portion 27. The communicating hole 43 is provided in the upper outer circumferential face between the first fluid conduit 28 and the second fluid conduit 29 of the multi-lumen tube 26. Two communicating holes 44 are provided. The first fluid conduit 28 is arranged between one of the communicating holes 44 and the communicating hole 43, and the second fluid conduit 29 is arranged between the other communicating hole 44 and the communicating hole 43.

The length and width dimensions in the circumferential direction of the communicating holes 43 and 44 are set so that an opening area of the communicating hole 43 is less than a distal end face area of the distal end portion 7 of the endoscope 2 or so that the perimeter of the opening of the communicating hole 43 is shorter than the perimeter of the distal end portion 7. Thus, the insertion portion 4 of the endoscope 2 is prevented from protruding to outside from the hole for an endoscope insertion portion 27 of the cleaning sheath 3A through the communicating hole 43.

The other components are the same as in the first embodiment, and like members are denoted by like reference numerals and a description of such members is omitted hereunder.

In a state in which the insertion portion mounting section 23 of the cleaning sheath 3A is mounted to the insertion portion 4, the sheath bending portion 40G covers the circumference of the bending portion 8 similarly to the first embodiment. According to the present embodiment, when the surgeon appropriately operates the bending knob 10, the bending portion 8 that is covered by the multi-lumen tube 26 of the cleaning sheath 3A bends in the upward direction or downward direction accompanying the operation of the bending knob 10.

In the present embodiment also, since the communicating hole 43 of the sheath bending portion 40G that covers the circumference of the bending portion 8 is positioned in the upper direction of the bending portion 8, and the thin-walled region 26b is positioned in the lower direction thereof, a bending operation of the bending portion 8 can be smoothly performed by operating the bending knob 10. In addition, the occurrence of a meandering portion on the inner circumferential side of the bending portion 8 can be prevented.

Further, the resistance of the thick-walled region 26a of the multi-lumen tube 26 is decreased by means of the communicating holes 43 and 44 and the wall thickness of the fluid conduits 28 and 29 that are disposed at positions that are different from the bending direction of the bending portion 8 is secured. Accordingly, when the bending portion 8 is bent in the upward direction, if slackness or creasing occurs between the communicating hole 43 and communicating holes 44 of the multi-lumen tube 26 disposed on the inner circumferential side of the bending portion 8, the fluid conduits 28 and 29 are shifted to the communicating hole 43 side or the communicating holes 44 side accompanying the occurrence of creasing, and crushing of the fluid conduits 28 and 29 can be prevented.

Figure 15:
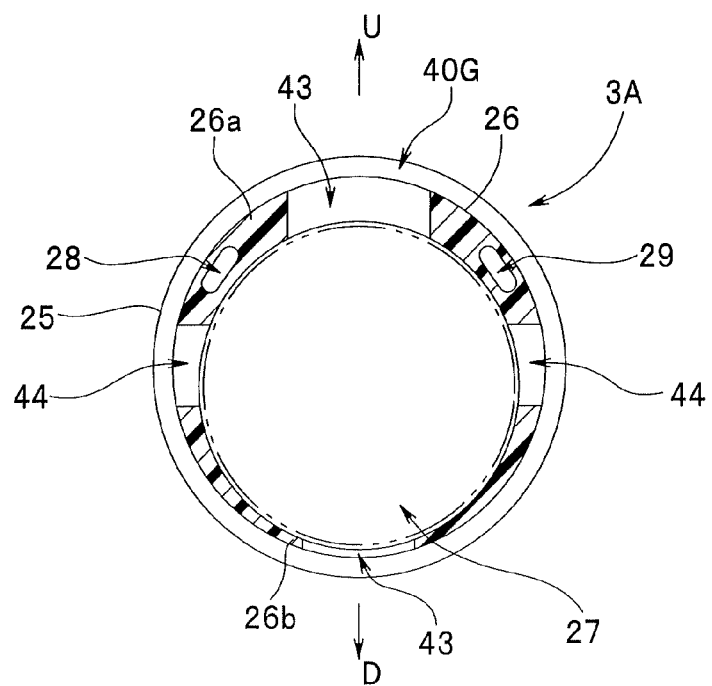
FIG. 15 is a cross-sectional view that illustrates a sheath bending portion in which a communicating hole is provided in a lower part that faces a communicating hole provided in an upper direction between conduits of a multi-lumen tube.

A configuration may also be adopted in which a communicating hole 43 that decreases a force amount is provided in the upper outer circumferential face between the first fluid conduit 28 and the second fluid conduit 29 that is the thick-walled region 26*a* of the multi-lumen tube 26 and, as shown in FIG. 15, on the thin-walled region 26*b* side, a communicating hole 43 is provided in the lower outer circumferential face below the bending portion 8 at a position facing the communicating hole 43 provided on the upper side to thereby decrease the cross-sectional area of the tube itself.

Thus, when the bending portion 8 is bent, a force that attempts to push and contract the multi-lumen tube 26 that arises on the inner circumferential side of the bend and a force that attempts to expand the multi-lumen tube 26 that arises on the outer circumferential side of the bend can be simultaneously reduced, and an effect can be exerted that reduces the load applied to the bend to the maximum degree.

In this connection, the configuration of the sheath bending portion 40G is not limited to a configuration in which the communicating holes 43 and 44 are provided parallel to the longitudinal axis as described above, and the sheath bending portion 40G may have the same configuration as a sheath bending portion that is illustrated in FIG. 16 to FIG. 21 as described hereunder.

A configuration example of the sheath bending portion is described hereunder referring to the drawings.

Figure 16:
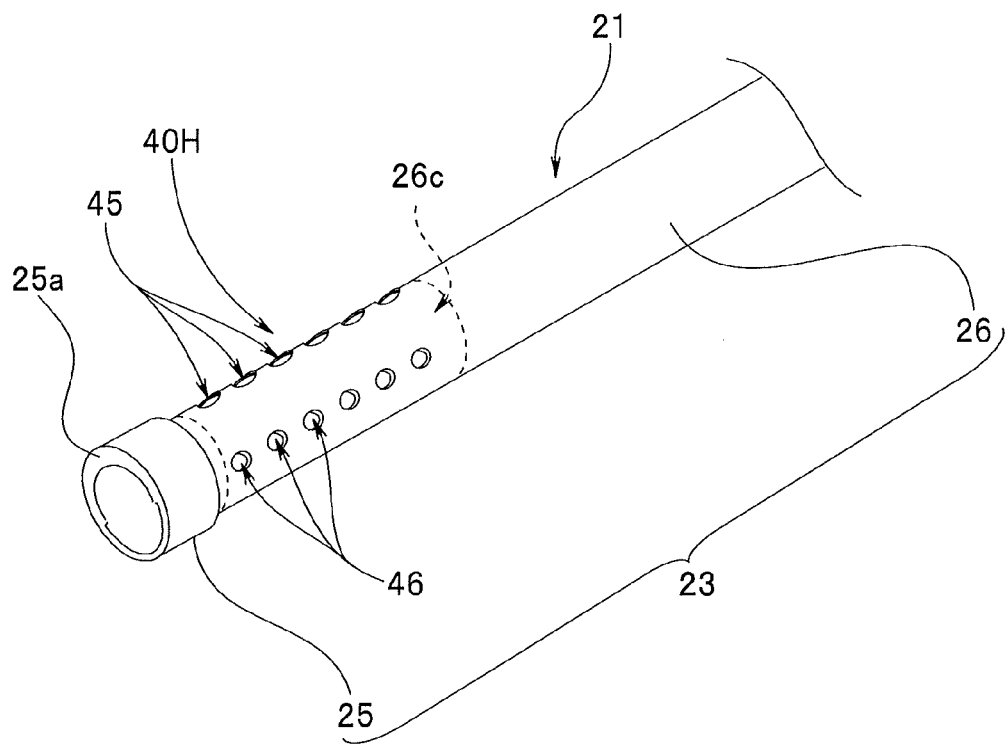
FIG. 16 to FIG. 18 relate to a modification example of the sheath bending portion.
Figure 17:
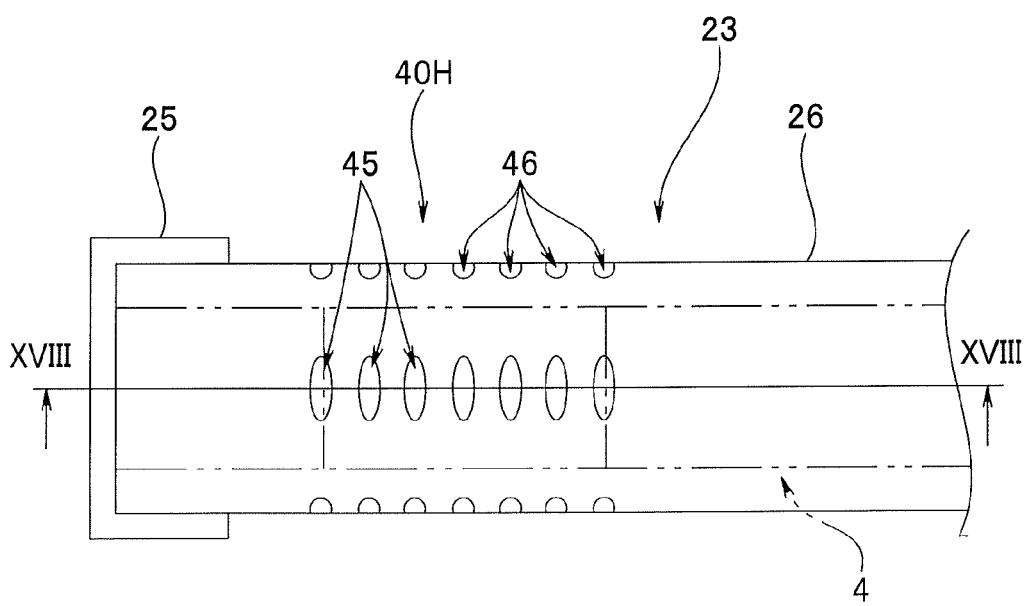
Figure 18:
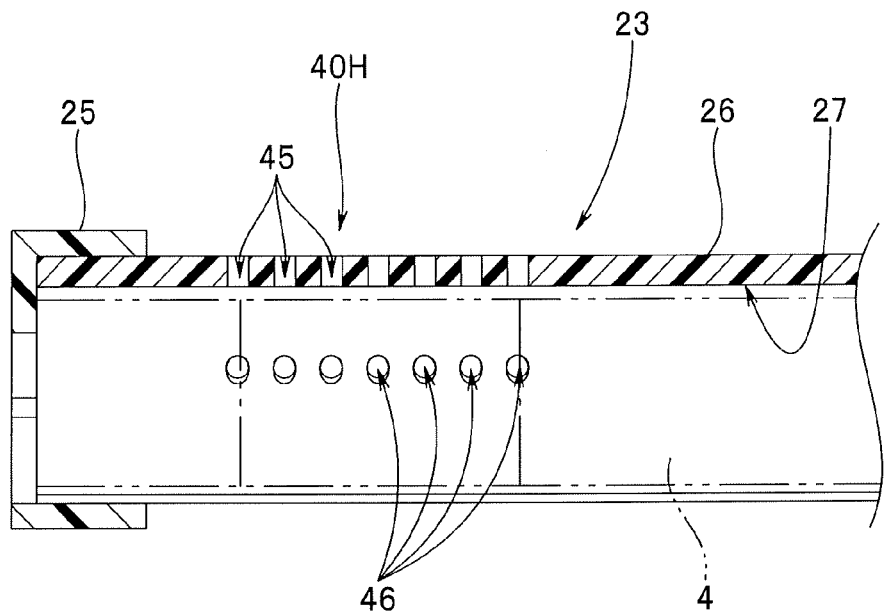

FIG. 16 to FIG. 18 relate to a modification example of the sheath bending portion. FIG. 16 is a perspective view that illustrates a sheath bending portion in which a plurality of communicating holes are arranged. FIG. 17 is a view of an insertion portion mounting section as seen from the upper direction. FIG. 18 is a cross-sectional view along a line XVI-XVI in FIG. 17.

As shown in FIG. 16 to FIG. 18, a sheath bending portion 40H of the present modification example includes a plurality of communicating holes 45 that are elongated in the circumferential direction instead of the communicating hole 43 that is a long hole parallel to the longitudinal axis. The sheath bending portion 40H also includes a plurality of communicating holes 46 that are elongated in the circumferential direction instead of the communicating holes 44 that are long holes parallel to the longitudinal axis. The plurality of communicating holes 45 and 46 are respectively arranged, for example, at regular intervals parallel to the longitudinal axis.

Thus, a plurality of communicating holes 45 that are elongated in the circumferential direction and are parallel to the longitudinal axis are provided in the upper outer circumferential face of the multi-lumen tube 26, a plurality of communicating holes 46 are provided so as to sandwich the fluid conduit 28 between the communicating holes 45 and the communicating holes 46, and a plurality of communicating holes 46 are provided so as to sandwich the fluid conduit 29 between the communicating holes 45 and the communicating holes 46. Therefore, when a compressive force acts on the multi-lumen tube 26 disposed on the inner circumferential side of the bending portion 8, the plurality of communicating holes 45 and the plurality of communicating holes 46 respectively absorb and decrease the force applied to the multi-lumen tube 26 so that the occurrence of creasing or a meandering portion can be prevented. As a result, treatment instruments no longer stick in a meandering portion. Further, when extracting the endoscope 2 from a trocar, a creased portion does not stick to the mouth of the trocar.

Figure 19:
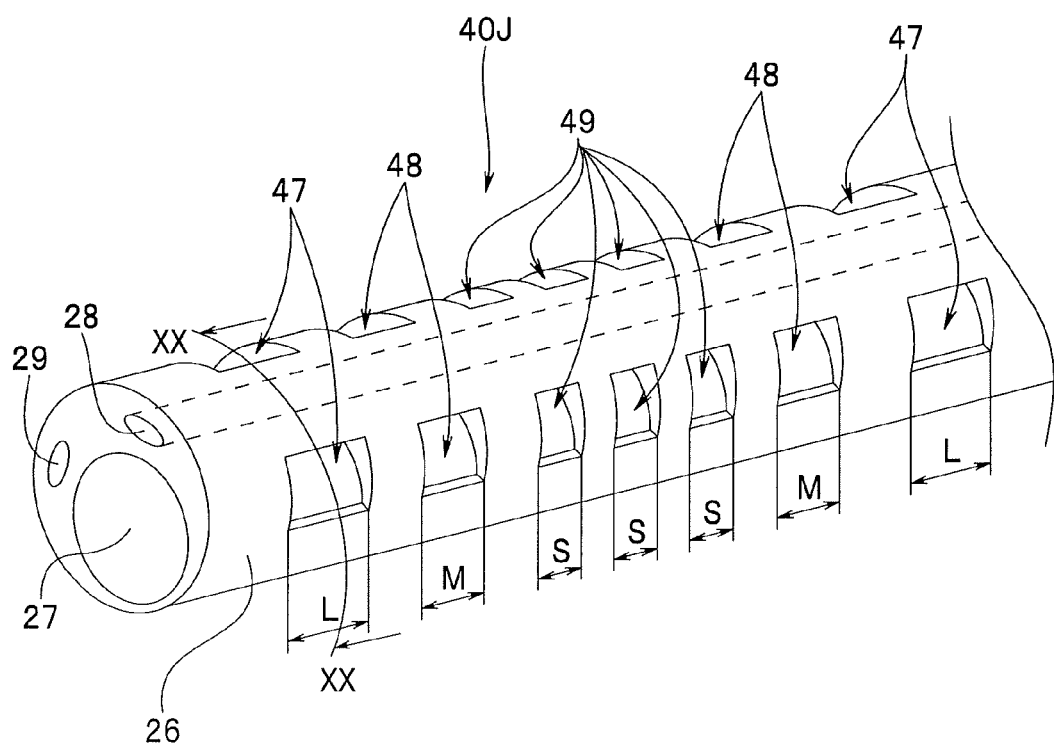
FIG. 19 to FIG. 21 relate to another modification example of the sheath bending portion.
Figure 20:
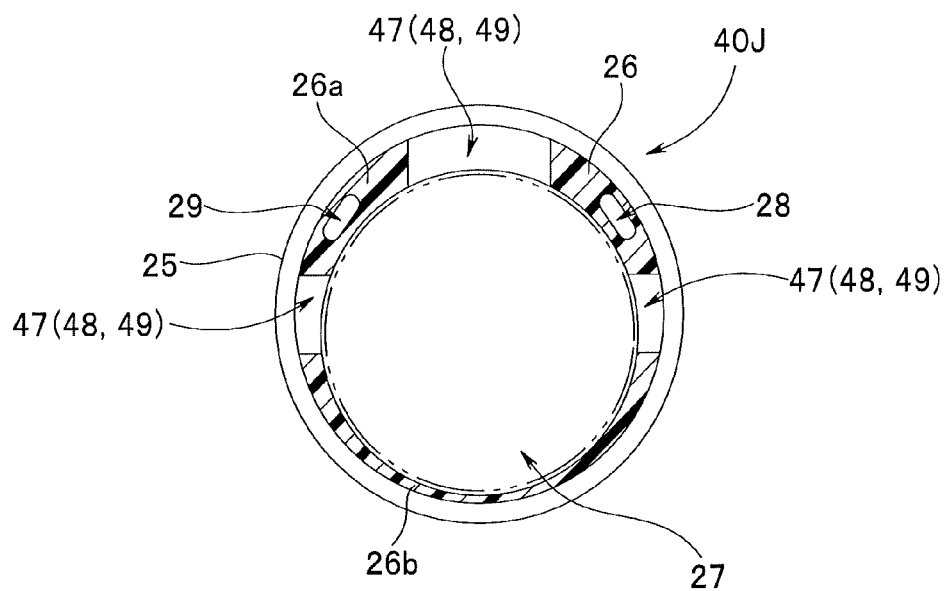
Figure 21:
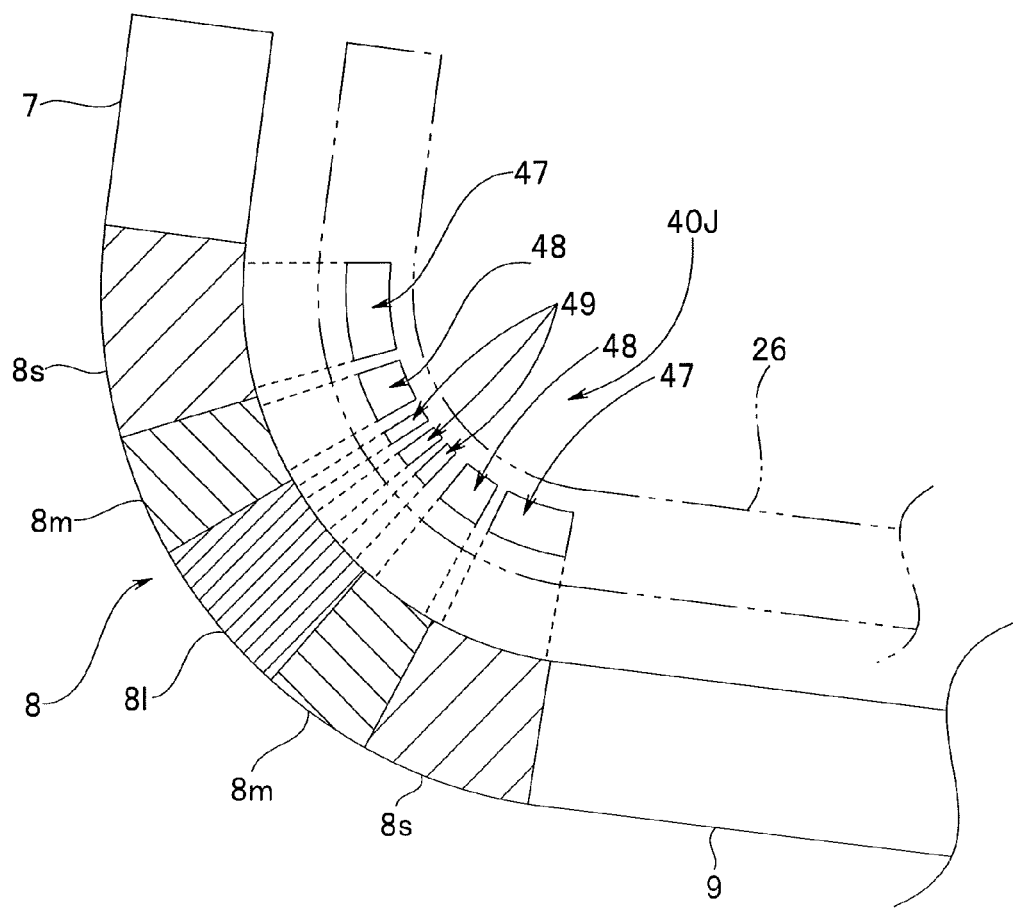

FIG. 19 to FIG. 21 relate to another modification example of the sheath bending portion. FIG. 19 is a perspective view that illustrates a sheath bending portion in which a plurality of communicating holes are arranged that have different length dimensions in the longitudinal direction. FIG. 20 is a cross-sectional view along a line XX-XX in FIG. 19. FIG. 21 is a schematic diagram that illustrates the relation between the curvature of a bending portion and the plurality of kinds of communicating holes provided in the sheath bending portion.

A sheath bending portion 40J of the present modification example includes, for example, three kinds of communicating holes 47, 48, and 49 that have different length dimensions in the longitudinal direction as shown in FIG. 19 and FIG. 20. The length dimensions in the longitudinal direction of first communicating holes 47 are set as the longest dimensions. The length dimensions in the longitudinal direction of third communicating holes 49 are set as the shortest dimensions. The length dimensions in the longitudinal direction of second communicating holes 48 are set so as to be shorter than the length dimensions of the first communicating holes 47 and longer than the length dimensions of the third communicating holes 49.

As shown in FIG. 21, the communicating holes 47, 48, and 49 are arranged at regular intervals parallel to the longitudinal axis in consideration of the curvature of the bending portion 8. More specifically, it is desirable that communicating holes arranged in a bending portion 81 that has the largest curvature (1/r) in the bending portion 8 are holes that prevent creasing occurring when the area or the perimeter of the communicating holes changes shape significantly due to deformation. Consequently, the third communicating holes 49 are provided at positions corresponding to the bending portion 81. Thus, in a region in which the bending portion 8 has a large curvature, a significant deformation of the third communicating holes 49 of the sheath bending portion 40J is prevented so that the occurrence of slackness or creasing at the circumference thereof can be prevented.

On the other hand, the first communicating holes 47 are provided at bending portions 8*s* that have the smallest curvature in the bending portion 8. Because the curvature at the bending portions 8*s* is small, a change in shape in the area or perimeter of the first communicating holes 47 is small. The second communicating holes 48 are provided at intermediate bending portions 8*m* that have a curvature that is greater than the bending portions 8*s* that have the smallest curvature and is less than the bending portion 81 that has the largest curvature.

By disposing the plurality of communicating holes 47, 48, and 49 whose length dimensions in the longitudinal direction are set based on the curvature of the bending portion 8 in this manner, it is possible to prevent the occurrence of a meandering portion in the sheath bending portion 40J that is positioned on the inner circumferential side of the bending portion 8 and also reduce the bending resistance.

Note that, in the embodiments illustrated in FIG. 16 to FIG. 21, a configuration may also be adopted that reduces the cross-sectional area of the tube itself by providing the communicating hole 43 at a lower part of the bending portion 8 opposite to the concave portion 41, as shown in FIG. 15, on the thin-walled region 26*b* side.

It should be understood that the present invention is not limited only to the above described embodiments, and various changes and modifications thereof could be made without departing from the spirit or scope of the invention.

What is claimed is:
1. An endoscope cleaning sheath, comprising:
a flexible tube body that comprises a hole for an endoscope insertion portion through which an insertion portion having a bending portion included in an endoscope is inserted, a first fluid conduit that supplies a gas, and a second fluid conduit that supplies a liquid, the hole, the first fluid conduit and the second fluid conduit being through-holes that are parallel to a longitudinal axis of the flexible tube body; and a cylindrical distal end nozzle that is provided at a distal end portion of the flexible tube body and that sprays at least one of the gas supplied through the first fluid conduit and the liquid supplied through the second fluid conduit at least at an observation window provided at a distal end portion of the insertion portion of the endoscope;

wherein:

the flexible tube body comprises a thin-walled region and a thick-walled region that are configured by arranging a central axis of the hole for an endoscope insertion portion to be eccentric in a predetermined direction of an orthogonal axis orthogonal to a central axis of the flexible tube body which is the longitudinal axis of the flexible tube body, the thin-walled region having a first wall thickness and a first cross-sectional area, and the thick-walled region having a second wall thickness and a second cross-sectional area wherein the first wall thickness and the first cross-sectional area are less than the second wall thickness and the second cross-sectional area;

the first fluid conduit and the second fluid conduit are provided in the thick-walled region at positions symmetrical with the orthogonal axis therebetween in a direction that is different from a bending direction of the bending portion of the insertion portion that is inserted and disposed in the hole for an endoscope insertion portion;

the thick-walled region of a sheath bending portion includes a first communicating hole provided between the first fluid conduit and the second fluid conduit to allow an outside of the flexible tube body to communicate with an inside of the hole, and a second communicating hole radially spaced from the first communicating hole with the first fluid conduit disposed therebetween, and a third communicating hole radially spaced from the first communicating hole with the second fluid conduit disposed therebetween; and the first, second and third communicating holes each comprise a proximally spaced communicating hole and a distally spaced communicating hole in the sheath bending portion of the flexible tube body, wherein a perimeter of the distally spaced communicating hole is greater than a perimeter of the proximally spaced communicating hole for each of the first, second and third communicating holes, wherein a distal portion of the sheath bending portion containing the distally spaced communicating holes exhibits decreased bending resistance with respect to a proximal portion of the sheath bending portion containing the proximally spaced communicating holes.

* * * * *